(12) United States Patent
Karageozian et al.

(10) Patent No.: US 7,977,385 B2
(45) Date of Patent: Jul. 12, 2011

(54) AGENTS FOR CORNEAL OR INTRASTROMAL ADMINISTRATION TO TREAT OR PREVENT DISORDERS OF THE EYE

(75) Inventors: Vicken H. Karageozian, Laguna Beach, CA (US); David Castillejos, Chula Vista, CA (US); John Park, Santa Ana, CA (US); Gabriel Arthuro Carpio Aragon, Tijuana (MX); Jose Luis Gutierres Floress, Tijuana (MX)

(73) Assignee: Numoda Biotechnologies, Inc., Philadelphia, PA (US)

( * ) Notice: Subject to any disclaimer, the term of this patent is extended or adjusted under 35 U.S.C. 154(b) by 401 days.

(21) Appl. No.: 10/389,226

(22) Filed: Mar. 14, 2003

(65) Prior Publication Data

US 2004/0043082 A1    Mar. 4, 2004

Related U.S. Application Data

(63) Continuation-in-part of application No. 10/215,680, filed on Aug. 9, 2002, now Pat. No. 7,008,960, which is a continuation of application No. 09/517,798, filed on Mar. 2, 2000, now Pat. No. 6,462,071.

(60) Provisional application No. 60/363,979, filed on Mar. 14, 2002.

(51) Int. Cl.
*A61K 31/17* (2006.01)
(52) U.S. Cl. .......................................... 514/588; 514/912
(58) Field of Classification Search .................. 514/588, 514/912
See application file for complete search history.

(56) References Cited

U.S. PATENT DOCUMENTS

| | | | |
|---|---|---|---|
| 4,409,205 A | 10/1983 | Shively | |
| 5,110,493 A | 5/1992 | Cherng-Chyi et al. | |
| 5,292,509 A | 3/1994 | Hageman | |
| 5,441,984 A | 8/1995 | Heath, Jr. et al. | |
| 5,470,881 A | 11/1995 | Charlton et al. | |
| 5,474,985 A | 12/1995 | Polansky et al. | |
| 5,554,187 A | 9/1996 | Rizzo, III | |
| 5,626,865 A | 5/1997 | Harris et al. | |
| 5,629,344 A | 5/1997 | Charlton et al. | |
| 5,866,120 A | 2/1999 | Karageozian et al. | |
| 5,891,084 A | 4/1999 | Lee | |
| 5,891,913 A | 4/1999 | Sallmann et al. | |
| 6,039,943 A | 3/2000 | Karageozian et al. | |
| 6,132,735 A | 10/2000 | Harris et al. | |
| 6,242,468 B1 | 6/2001 | Li et al. | |
| 6,335,348 B1 | 1/2002 | Ross et al. | |
| 6,384,056 B1 | 5/2002 | Ross et al. | |
| 6,395,758 B1 | 5/2002 | Ross et al. | |
| 6,399,648 B1 | 6/2002 | Ross et al. | |
| 6,506,788 B1 | 1/2003 | Ross et al. | |
| 6,551,590 B2 | 4/2003 | Karageozian et al. | |
| 2001/0053347 A1* | 12/2001 | Varani et al. | 424/59 |

FOREIGN PATENT DOCUMENTS

| | | |
|---|---|---|
| EP | 0244178 A2 | 11/1987 |
| WO | 0009105 A2 | 2/2000 |
| WO | 0051620 A1 | 9/2000 |
| WO | 03068166 A2 | 8/2003 |

OTHER PUBLICATIONS

Hayreh (Exp Review, Opthamol. 2(6), (2007) 889-894.
International Search Report Issued Aug. 20, 2003 in Int'l Application No. PCT/US03/04617.
International Search Report Issued Jul. 13, 2000 in Int'l Application No. PCT/US00/05587.
EP Supplemental Search Report issued Oct. 20, 2004 in EP Application No. 00916034.
International Search Report Issued Aug. 15, 2003 in Int'l Application No. PCT/US03/07700.
EP Supplemental Search Report Issued Mar. 8, 2005 in EP Application No. 03709127.
EP Supplemental Search Report issued Apr. 11, 2005 in EP Application No. EP03711552.
Allen, et al., "Nitric oxide synthase inhibitors exert differential time-dependent effects on LPS-induced uveitis", Exp. Eye Res. Jan. 1996; 62(1):21-8 (Abstract only).
Kawashima, et al., "Effects of mitomycin C on the rat retina", Documenta Ophthalmologica 92: 229-241, 1996.
Kawamura, et al., "Effects of an anti-prostaglandin agent added to the irrigation solution on damage to the anterior segment in monkey eyes induced by pars plana vitrectomy", Nippon Ganka Gakkiai Zasshi, Aug. 1989;93(8):823-9 (Abstract only).

* cited by examiner

*Primary Examiner* — Zohreh Fay
(74) *Attorney, Agent, or Firm* — Panitch Schwarze Belisario & Nadel LLP

(57) ABSTRACT

Methods and preparations for treating disorders of the eye and/or causing dissolution of corneal proteoglycans and organized healing of corneal stroma, softening of the cornea for non-surgical refractive correction of eyesight, removing corneal haze and opacification, inhibiting fibroblasts and preventing corneal fibrosis and scar formation, treating pterigiums and treating corneal neovascularization as well as iris neovascularization. Preparations containing a) urea, b) urea derivatives (e.g., hydroxyurea, thiourea), c) antimetabolites, e) urea, urea derivatives, non-enzymatic proteins, nucleosides, nucleotides and their derivatives (e.g., adenine, adenosine, cytosine, cytadine, guanine, guanitadine, guanidinium, guanidinium chloride, guanidinium salts, thymidine, thymitadine, uradine, uracil, cysteine), reduced thioctic acid, uric acid, calcium acetyl salicylate, ammonium sulfate, isopropyl alcohol, ethanol, polyethylene glycol, polypropylene glycol or other compound capable of causing nonenzymatic dissolution of the corneal protoeglycans or f) any of the possible combinations thereof, are administered to the eye in therapeutically effective amounts.

10 Claims, No Drawings

AGENTS FOR CORNEAL OR INTRASTROMAL ADMINISTRATION TO TREAT OR PREVENT DISORDERS OF THE EYE

CROSS-REFERENCE TO RELATED APPLICATIONS

This application claims priority to U.S. Provisional Application 60/363,979 filed on Mar. 14, 2002, which is expressly incorporated herein by reference. This application is also a continuation-in-part of copending U.S. patent application Ser. No. 10/215,680 entitled Agents for Intavitreal Administration To Treat or Prevent Disorders of the Eye filed on Aug. 9, 2002, which is a continuation of U.S. patent application Ser. No. 09/517,798 filed on Mar. 2, 2000 and now issued as U.S. Pat. No. 6,462,071 B1.

FIELD OF THE INVENTION

The present invention relates generally to pharmaceutical preparations and medical treatment methods, and more particularly agents (i.e. Urea, Urea derivatives, non-steroidal anti-inflammatory drugs and Anti-metabolite drugs) used alone or in combinations with each other (or with other agents) to treat or prevent certain disorders of the eye.

BACKGROUND OF THE INVENTION

Prior Ophthalmologic Uses of Urea

U.S. Pat. Nos. 5,629,344 (Chariton) and 5,470,881 (Chariton) describe certain therapeutic applications of urea preparations to the eye. These prior patents specifically describe non-aqueous ointments and other non-aqueous preparations of urea for use in the eye, pointing out that aqueous solutions of urea were believed to be impractical for use in the eye. For example, these prior patents state as follows: "One of the reasons urea has not been used in treating eye disorders is that it will hydrolyze in aqueous vehicles thus producing ammonia as a byproduct. Ammonia is toxic to the eye, and thus urea in an aqueous solution would be impractical for use as an ophthalmic medicament." Thus, prior to Applicant's invention, aqueous solutions of urea or urea derivatives were thought to be unstable and potentially toxic to the eye.

Anatomic and Physical Properties of the Cornea

The cornea is the first and most powerful refracting surface of the optical system of the eye. Production of a sharp image at the retinal receptors requires that the cornea be transparent and of the appropriate refractive power. The average corneal thickness of a normal cornea is 0.56 mm in persons under 25 years of age; this thickness slowly increases with age to become 0.57 in persons over 65 years of age. The cornea is somewhat thicker in the periphery than the center. The thickness of the cornea is greatest after the eyes have been closed for some time, as after sleeping, this thickness decreases slightly when the eyes are opened and exposed to the dehydrating effects of the air.

The cornea is composed of six layers: a) Epithelium. b) Basement membrane. c) Bowman's membrane. d) Stroma. e) Descemet's membrane. f) Endothelium.

a) Epithelium: The epithelium consists of 5-6 layers of cells. The most superficial cells are flat overlapping squamous cells. The middle layer consists of cells that become more columnar as the deeper layers are approached. The innermost layer (basal) is made up of columnar cells packed closely together. All the cells are held together by a cement substance. Also, the cell surfaces form processes that are fitted into corresponding indentations of adjacent cells and connected in places by attachment bodies called desmosomes. The basal cells are connected to the basement membrane by hemidesmosomes. The epithelium represents 10% of the total wet weight of the cornea. Water in the epithelium represents 70% of the wet weight.

Although the epithelium consists of 5-6 layers of cells, the healthy epithelium is very strongly attached to each other by desmosomes as well as to the Basement membrane by hemidesmosomes.

b) Basement membrane: Between the columnar epithelial cells and Bowman's membrane is a basement membrane from 60-65 nm thick. The basement membrane has been examined histochemically and found to be similar to other basement membranes.

c) Bowman's membrane: Bowman's layer is a sheet of transparent tissue about 12 μm thick, without structure as seen by light microscopy. Under electron microscopy it appears to be made up of uniform fibrils, probably of collagenous material, running parallel to the surface. Bowman's layer possesses little resistance to any pathologic process, and is easily destroyed and never regenerates.

d) Stroma: The Stroma comprises about 90% of the whole cornea. The Stroma is composed of layers of lamellae, each of which runs the full length of the cornea; although the bundles interlace with one another, they are nearly parallel to the surface. The cell bodies, called keratocytes, are flattened, so they too lie parallel to the surface, and their cell processes interlace with one another. This arrangement of the fibers gives optical uniformity to the cornea. The Stroma comprises about 90% of the whole cornea. The Stroma is composed of differentiated connective tissue containing 75% to 80% water on a wet weight basis. The remaining solids 20% to 25% is collagen, other proteins, and glycosaminoglycans or mucopolysaccharides constitute the major part. The collagen fibrils are neatly organized and present the typical 64 to 66 nm periodicity of collagen fibrils separated from each other by the ground substance. The size, regularity, and precise spacing of the fibrillar structures are the physical characteristics essential for corneal transparency.

The glucosaminoglycans (GAG, mucopolysaccharides) represent 4% to 4.5% of the dry weight of the cornea. GAG are localized in the interfibrillar or interstitial space, probably attached to the collagen fibrils or to soluble proteins of the cornea. The GAG plays a role in corneal hydration through interaction with electrolytes and water. Three major GAG fractions are found in the corneal Stroma: keratin sulfate (50%), chondroitin (25%), and chondroitin sulfate A (25%). GAG's have been implicated in the maintenance of the corneal hydration level and transparency.

e) Descemet's Membrane: Is made of type IV collagen, unlike the corneal Stroma, there are no significant amounts of sulfated GAG in the Descemet's membrane. The collagen in this membrane is insoluble except in strong alkali or acid and is more resistant to collagenase than corneal stroma collagen. Jakus[2] has observed with the electron microscope that this membrane has collagen like structure of great regularity. Descemet's membrane is highly elastic and represents a barrier to perforation in deep corneal ulcers.

f) Endothelium: The endothelium is a single layer of cells lining Descemet's membrane. Its inner surface is bathed by the aqueous humor. In humans the endothelium cell layer has limited, if any, reproductive capacity. Aging causes cell loss, and the remaining cells enlarge and spread so that Descemet's membrane remains completely covered.[6] therefore endothelial cell density, expressed as cells per unit area, decreases with age. Similarly, cell loss from trauma, inflammation, or surgery is compensated for by increased cell size and decreased cell density.

Corneal metabolism embraces a series of chemical processes by which energy is obtained and utilized for the normal functions of the cornea. In the cornea, energy is needed for maintenance of its transparency and dehydration. Energy in the form of ATP is generated by the breakdown of glucose into lactic acid and into carbon dioxide and water (i.e., Krebs Cycle). The cornea obtains glucose mainly from the aqueous humor. The tears and limbal capillaries appear to contribute minimal amounts of glucose and Oxygen for corneal metabolism.

Most of the oxygen consumed by the cornea is taken in by the epithelium and the endothelium. The oxygen consumption of the epithelium and endothelium can be approximately 26 times that of the stroma. The corneal endothelium gets most of its required oxygen from the aqueous humor, while the corneal epithelium gets much of its oxygen from either the capillaries at the limbus or from the oxygen dissolved in the pre-corneal film.

Methods for the Refractive Correction of the Eye:

Radial keratotomy (RK) is a surgical procedure to improve myopia by changing the corneal curvature. This is achieved by making several deep incisions in the cornea in a radial pattern. The eye surgeon makes 4, 8, or 16 incisions so as to flatten the curvature of the central cornea, thus correcting the patient's vision. The main drawbacks of RK include, a) It can only be used to correct low levels of myopia. b) This surgical procedure cannot correct hyperopia. c) RK procedure seriously weakens the cornea and creates corneal scars. d) The corneal curvature changes are temporary and frequently continue to change with time.

Photorefractive keratectomy (PRK) is a surgical procedure that uses the excimer laser, which is controlled by a computer. With the PRK procedure, the excimer laser ablates and sculpts the corneal surface to the desired shape to correct the patient's vision. There are a combination of lasers with a combination of computer controls that can reliably treat myopia, hyperopia, and astigmatism. Since PRK is a surgical procedure, it can result in complications. Infection is the most serious complication resulting from the ablation of a large area of the corneal epithelium. In addition delayed corneal healing because of the absence of the corneal epithelium, corneal haze, corneal scarring, over correction or under-correction and development of astigmatism are other complications of PRK. These complications must be treated with medications or further surgery.

Laser in-situ keratomileusis[11] (LASIK) is a surgical procedure that is a variation on PRK involving an excimer laser and a precise cutting tool called a microkeratome. The microkeratome is used to make a 150-175 micron circular flap of the cornea. The circular flap is flipped back, as if on a hinge, to expose the stromal layer of the cornea. With the flap folded back, the refractive eye surgeon now ablates the stroma and makes the refractive correction using the excimer laser. The circular corneal flap is repositioned on the ablated cornea to complete the procedure. With a precision laser treatment and normal reattachment and healing of the corneal flap, the refractive results of good vision correction are very rapid. There is, however, a significant list of potential complications and risks associated with LASIK procedure; failure of the microkeratome to leave a hinge on the corneal flap with the first incision, loss of the corneal flap after the operation, slipping of the flap and healing off center, first incision is too deep or too shallow, corneal epithelium ingrowths into the stroma, infection of the cornea, corneal ectasia, loss of visual acuity from scarring and optical distortion of the collagen structure of the stroma.

Laser epithelial keratomileusis (LASEK) is a surgical procedure that is a variation on PRK involving an excimer laser that combines the advantages and eliminates the disadvantages of PRK and LASIK. A 7.0 mm circular area of the epithelium is marked with a Hoffer trephine centered over the pupil. The corneal epithelium is removed by using a blunt spatula, or is exposed to 20% isopropyl alcohol solution which allows the corneal epithelium to be peeled off. Using the excimer laser the surgeon ablates and sculpts the corneal surface to the desired shape to correct the patient's vision. At the end of the procedure the corneal epithelial flap created by the alcoholic solution is placed back onto the ablated cornea, a drop of antibiotic, a drop of non-steroidal anti-inflammatory agent and a therapeutic contact lens is applied to the corrected eye. The epithelial defect created by the scrapping of the corneal epithelium, or by peeling of the epithelium after the application of alcoholic solution is completely closed within a few days. With a precision laser treatment and normal healing of the corneal epithelium, the refractive results of good vision correction are very rapid. There are, however, a few potential complications and risks associated with LASEK procedure; infection of the cornea because of the epithelial defect as a result of epithelial scrapping, use of alcoholic solution causes extensive damage to the peeled corneal epithelium minimizing the benefits of the reapplied corneal epithelium.

Thermokeratoplasty is another corneal reshaping method. In this procedure heat at 55° C. to 58° C. is applied to the collagen fibers of the cornea to induce shrinkage without the destruction of the tissue. The shrinkage of the collagen fibers result in the change of the mechanical properties and flattening of the cornea, thus achieving refractive correction. U.S. Pat. No. 4,881,543 describes the use of microwave electromagnetic energy to shrink the collagen of the cornea. U.S. Pat. No. 5,779,696 describes the use of light energy to reshape the cornea. All of these systems of Thermokeratoplasty have a shortcoming that is the treated corneas are unstable after the treatment.

Orthokeratology is a non-surgical procedure designed to correct refractive errors by reshaping the cornea to the corneal curvature required to achieve emmetropia. This is accomplished by applying a series of hard contact lenses that change the corneal curvature until the desired curvature is achieved. However once the desired curvature has been produced, retainer hard contact lenses must be worn to stabilize the results otherwise regression will occur.

Enzyme Orthokeratology is related to traditional Orthokeratology in that it is defined primarily as a contact lens procedure of correcting refractive errors of the eye by reshaping the cornea to the curvature required for emmetropia. The system is enhanced by enzymatically softening the cornea, and reshaping is obtained in a shorter period of time, and retainer lenses may not be required for good visual acuity after removal of the contact lens from the eye and regression will not be a problem.

Chemical Orthokeratology is related to traditional Orthokeratology in that it is defined primarily as a contact lens procedure of correcting refractive errors of the eye by reshaping the cornea to the curvature required for emmetropia. The system is enhanced by applying topically or by intra-stromal injection a chemical that is not an enzyme and softening the cornea, and reshaping is obtained in a shorter period of time, and retainer lenses may not be required for good visual acuity after removal of the contact lens from the eye and regression will not be a problem.

SUMMARY OF THE INVENTION

The present invention provides methods for treating or preventing disorders of the eye of a human or veterinary patient by administering topically onto the eye or by injection into the eye (e.g. intravitreal, intrastromal or sub-conjunctival injection) a therapeutically effective amount of an aqueous solution containing an agent selected from: urea, a urea derivative, non-enzymatic protein urea, non-enzymatic proteins, nucleosides, nucleotides and their derivatives (e.g., adenine, adenosine, cytosine, cytadine, guanine, guanitadine, guanidine, guanidinium chloride, guanidinium salts, thymidine, thymitadine, uradine, uracil, cysteine), reduced thioctic acid, uric acid, calcium acetyl salicylate, ammonium sulfate or other compounds capable of causing non enzymatic dissolution of the proteoglycans or any possible combination thereof. Included among the therapeutic purposes for which this method may be used are removal of the corneal epithelium, dissolution of the corneal proteoglycans, interface closure and organized healing of corneal stroma in refractive LASIK correction, dissolution of proteins and amino acids so as to compress the collagen fibrils for better visual acuity and better quality of vision, softening of the cornea prior to or during application of a contact lens or cornea-reshaping template for the non-surgical refractive correction of myopia, presbyopia, hyperopia, astigmatism and keratoconus, dissolution of newly synthesized proteoglycans thereby lessening or eliminating corneal haze and/or corneal opacification, dissolution of proteoglycans in the anterior chamber thereby increasing outflow of fluid which may lower of intra-ocular pressure in some glaucoma patients, causing a solvent action on fibroblasts, inhibiting fibroblasts, inhibiting or preventing corneal fibrosis and scar formation, inhibiting the proliferation of fibroblasts in ocular tissue, inhibiting VEGF activity in the cornea and the iris via an anti-angiogenic effect, thus eliminating both the progression and the regression of corneal new vessels and iris new vessels. By one or more of these therapeutic effects and/or other mechanisms of action yet to be elucidated, the method of the present invention may be usable to treat various disorders of the eye. As used in this patent application, the term "treat" shall not be limited only to treatment of existing diseases or disorders but also shall mean preventing, deterring, stopping, curing, or slowing the progression of such disorders. The disorders of the eye that may be treated by the method of the present invention include but are not limited to: refractive disorders, impaired visual acuity or diminished quality of vision, myopia, presbyopia, hyperopia, astigmatism, keratoconus, corneal fibrosis, scar formation, corneal opacities, pterigiums, corneal neovascularization, iris neovascularization, glaucoma.

Further in accordance with the invention, the agent may be administered in combination with an antimetabolite compound such as; mitomicyn, methotrexate, thiourea, hydroxyurea, 6-mercaptopurine, thioguanine, 5-fluorouracil, cytosine arabinoside and 5-azacytidine.

Still further in accordance with the invention, the agent may be administered in combination with an antineoplastic agent such as Actinomycin D, daunorubicin, doxorubicin, idarubicin, bleomycins, or plicamycin may also be used in combination with these anti-metabolites.

Still further aspects, objects and advantages of the invention will be apparent to those of skill in the art who read and understand the following detailed description of the invention and the specific examples set forth therein.

DETAILED DESCRIPTION

The following detailed description and the examples referred to therein are provided for the purpose of describing certain embodiments or examples of the invention only and shall not be construed as limiting the scope of the invention in any way.

Removal of the Corneal Epithelium

One example of an application of the method of the present invention is for the removal of corneal epithelium. As explained above, the corneal epithelial cells are held together by a cement substance. In addition the surfaces of the cells form processes that are fitted into the corresponding indentations of the adjacent cells and connected by attachment bodies called desmosomes. In addition the basal cells of the epithelium are connected to the basement membrane by hemidesmosomes. When the corneal epithelium is damaged by chemical or physical means, swelling of the stroma follows. Abrasion of the cornea or any condition leading to the loss of epithelium is likely to produce localized areas of corneal swelling and cloudiness and allows microbial access and bacterial infections. Fortunately, the corneal epithelium regenerates rapidly, and the excessive hydration and wound closure in the absence of bacterial infections is slight and transient.

Effecting mechanical or chemical de-epithelialization (debridement) while keeping the epithelium in tact an without damage is not an easy task. There are several methods that are utilized presently, but all these methods and materials cause severe damage to the corneal epithelium.

Mechanical de-epithelialization is typically performed under topical anesthesia with a local anesthetic with a blunt spatula after the epithelium is marked with a 7.0 mm Hoffer trephine centered over the pupil. The resulting corneal wound usually takes several days to re-epithelialize. During this time any exposed corneal incision or wound is susceptible to bacterial contamination and infection.

Chemical de-epithelialization using alcohol is also typically performed under topical anesthesia with a local anesthetic. The epithelium is marked, and by a gentle depression on the trephine a circular cut is made with a 7.0 mm Hoffer trephine centered over the pupil. While the trephine is in place 5-10 drops of 20% Isopropyl Alcohol are dispensed into the trephine and kept in contact with the epithelium for several minutes. The alcoholic solution is removed with a dry sponge, and the trephine is removed from the cornea. Using a blunt spatula the epithelium is removed intact in one piece. This procedure is a simple way to de-epithelialize the cornea, however 50%-70% of the epithelial cells are damaged because of the exposure to the alcoholic solution. Furthermore the 20% alcoholic solution is very irritating and inflammatory to the eye. After the surgical procedure, the resulting corneal wound is covered with the single piece of the alcohol removed epithelium. The resulting wound is temporarily covered with corneal epithelium which will take several days to re-epithelialize. During this time of wound healing the cornea is less susceptible to bacterial contamination and infection.

In accordance with the present invention, there is provided a new method for chemical removal of the corneal epithelium using an agent selected from: urea, a urea derivative, non-enzymatic protein urea, non-enzymatic proteins, nucleosides, nucleotides and their derivatives (e.g., adenine, adenosine, cytosine, cytadine, guanine, guanitadine, guanidine, guanidinium chloride, guanidinium salts, thymidine, thymitadine, uradine, uracil, cysteine), reduced thioctic acid, uric acid, calcium acetyl salicylate, ammonium sulfate or other compounds capable of causing non enzymatic dissolution of the proteoglycans or any possible combination thereof. This method may be performed under topical anesthesia with a local anesthetic. First, the epithelium is marked, and by a gentle depression on the trephine a circular cut is made with a 7.0 mm Hoffer trephine centered over the pupil. While the trephine is in place 5-10 drops of the agent (e.g., 0.01%-20% of aqueous urea solution) is dispensed into the trephine and kept in contact with the epithelium for several minutes. The agent (e.g., aqueous urea solution) is removed with a dry sponge, and the trephine is removed from the cornea. Using a blunt spatula the epithelium is removed intact in one piece. This procedure is a simple way to de-epithelialize the cornea resulting in no damage to the epithelial cells. After the surgical procedure, the resulting corneal wound is covered with the single piece of the urea removed epithelium. The resulting wound is temporarily covered with corneal epithelium which will re-epithelialize in 1-2 days. During this time of wound healing the cornea is less susceptible to bacterial contamination and infection. This chemical de-epithelialization of the cornea using an agent of the present invention (e.g., urea solution) may be useful as an adjunct to ophthalmic surgery for the treatment of herpetic epithelial keratitis, as well as for refractive correction of vision using the Laser epithelial keratomileusis (LESEK).

Enhanced Corneal Interface Closure and Organized Healing of the Corneal Stroma in Refractive LASIK Correction.

The present invention also provides methods for enhancing healing of the cornea after LASEK surgery. In this method, an agent selected from: urea, a urea derivative, non-enzymatic protein urea, non-enzymatic proteins, nucleosides, nucleotides and their derivatives (e.g., adenine, adenosine, cytosine, cytadine, guanine, guanitadine, guanidine, guanidinium chloride, guanidinium salts, thymidine, thymitadine, uradine, uracil, cysteine), reduced thioctic acid, uric acid, calcium acetyl salicylate, ammonium sulfate or other compounds capable of causing non enzymatic dissolution of the proteoglycans or any possible combination thereof, is applied topically to the cornea following a LASIK procedure. For example, a few drops of the agent (e.g., 0.01%-20.0% aqueous urea solution) may be placed onto the surface of the excimer laser ablated stroma before the cut flap of the corneal epithelium is repositioned on the laser ablated cornea. The urea solution placed at the interface of the corneal epithelium and stroma, will result in the localized solubilization of the stromal proteoglycans and will compress the collagen fibril packing for better visual performance, but normal transparency.

Successful completion of Laser in-situ keratomileusis (LASIK) refractive correction results in the precision cutting of the cornea, excimer laser ablation of the stroma and the repositioning of the circular flap on the ablated cornea. Normal reattachment and healing of the corneal flap are very important parameters for good vision correction and rapid healing. The superficial placement of the microkeratome cut circular flap of the cornea onto the excimer laser ablated stroma results in an interface gap in the stroma between the upper and lower parts of the stroma. This interface gap interferes with optimum vision correction, in addition the interface gap never completely comes together as a single stoma indicating the lack of complete wound healing of the cornea.

In the present invention of enhanced corneal interface closure and organized healing of the LASIK refractive corrected cornea, a few drops of an agent of the present invention (e.g., 0.01%-20.0% aqueous urea solution) is placed onto the surface of the excimer laser ablated stroma before the microkeratome cut flap of the cornea is repositioned on the laser ablated cornea. The urea solution placed at the interface of the two corneal flaps will result in the localized solubilization of the stromal proteoglycans and eliminate the interface gap, thus producing optimum vision correction. In addition the localized solubilization of the proteoglycans of the stroma will result in the compression of the collagen fibril packing for better visual performance, but normal transparency.

Softening of the Corneal Stroma by Topical or Intrastromal Application, for the Non-Surgical Refractive Correction of Myopia, Presbyopia, Hyperopia, Astigmatism and Keratoconus The present invention also provides methods for softening the cornea by administering to the cornea an agent selected from: urea, a urea derivative, non-enzymatic protein urea, non-enzymatic proteins, nucleosides, nucleotides and their derivatives (e.g., adenine, adenosine, cytosine, cytadine, guanine, guanitadine, guanidine, guanidinium chloride, guanidinium salts, thymidine, thymitadine, uradine, uracil, cysteine), reduced thioctic acid, uric acid, calcium acetyl salicylate, ammonium sulfate or other compounds capable of causing non enzymatic dissolution of the proteoglycans or any possible combination thereof, in an amount that is effective to cause temporary softening of the cornea so that it can be reshaped from a first configuration to a desired second configuration of emmetropia. The softening of the cornea could take place while the patient is wearing rigid contact lenses having a concave shape of the desired second configuration rendering the eye emmetropic. The cornea is thereafter permitted to shape to the desired second configuration under the influence of the lens. Since the corneal softening is a result of localized solubilization of the proteoglycans and not the chemical breakdown of the of the proteoglycan molecules, it is possible that the corneal softening effect of the agent will dissipate much faster in the presence or absence of the molding rigid lens.

The shape of the cornea is based on the collagen fibrils of the stroma which are held in place at a much specified distance from each other in parallel along with the mucopolysaccharides cement layers between these collagen fibrils. The Urea and Urea derivatives have the ability of solubilizing the mucopolysaccharides as well as various proteins. The stroma is therefore softened and becomes more pliable and easy to mold to a more desirable shape.

In the preferred embodiment, the cornea softening agent comprises urea or a urea derivative together with pharmaceutically acceptable carriers and additives. The preparation may be supplied in a liquid or lyophilized form. The cornea softening agent in accordance with the present invention is administered to the cornea in a number of ways. Typically, the agent is administered either directly in the form of eye drops, or by the use of a corneal softening agent delivery vehicle, which may include special drug delivery systems including liposomes, sustained release gels and implantable solid dosage forms as well as contact lens and biodegradable corneal collagen shield.

Non-Surgical Treatment and Elimination of Corneal Haze and Corneal Opacification A reduction of visual acuity and blindness may result from a lack of corneal clarity caused by corneal traumas, corneal scars, or any other cause of corneal opacification. Patients who have a reduction of visual acuity as a result of corneal opacities are estimated to be three million. The current treatment for corneal opacity is corneal transplantation using a surgical procedure called penetrating lamellar keratoplasty (PKP), using human corneal donor tissue. This surgical technique is considered safe and effective, however one of the risks includes graft rejection as well as viral and bacterial infections transmitted through the donor corneal tissue. The overall number of transplant surgical procedures that can be performed is limited by the availability of donor corneas for transplantation.

The present invention provides methods for improving corneal clarity or treating corneal scars, corneal opacification, and optical aberrations including corneal haze by administering to the eye an agent selected from: urea, a urea derivative, non-enzymatic protein urea, non-enzymatic proteins, nucleosides, nucleotides and their derivatives (e.g., adenine, adenosine, cytosine, cytadine, guanine, guanitadine, guanidine, guanidinium chloride, guanidinium salts, thymidine, thymitadine, uradine, uracil, cysteine), reduced thioctic acid, uric acid, calcium acetyl salicylate, ammonium sulfate or other compounds capable of causing non enzymatic dissolution of the proteoglycans or any possible combination thereof, in an amount that is effective to accelerate the solubilization of corneal proteoglycans, mucopolysaccharides and various other proteins and lead to the reorganization of corneal collagen. The resulting reorganization will clear corneal scars, corneal opacities and corneal haze. For example, the agent (e.g., an aqueous solution of urea or a urea derivative) may be administered topically or by injection in an amount that reduces corneal collagen disorganization by chemical modification or dissolution of corneal stromal glycoprotein's and proteoglycans.

The role of corneal glycoprotein's and proteoglycans in the establishment and maintenance of corneal transparency is not well understood. Stromal proteoglycans have been hypothesized to play a role in the regulation of collagen fiber spacing. Although the precise role of proteoglycans is still unclear, they are thought to influence the hydration, thickness and clarity of the cornea. The functional significance of hyaluronan in the cornea, except during development and in some corneal abnormalities is still unknown.

In some opaque human corneal scars, the scars have been found to contain collagen fibrils with abnormally large diameter and irregular interfibrillar spacing. However, during wound healing of rabbit corneas, the early opaque scars contain collagen fibrils of generally normal diameter that are irregularly spaced within the tissue. The collagen fibril diameter does not markedly change after a year of healing, but the spacing between the fibrils returns to normal and there is a concomitant decrease in the opacity of the scar.

In a 1983 paper authored by Hassell et al., showed that opaque scars that contained the large interfibrillar spaces also contained unusually large chondroitin sulfate proteoglycans with glycosaminoglycan side chains of normal size. These opaque scars also lacked the keratan sulfate proteoglycan but did contain hyaluronic acid. The biochemical analysis of proteoglycans in rabbit corneal scars in corneal wounds compared to normal cornea adjacent to the scar demonstrates that the areas synthesize proteoglycans measurably different from one another.

Hassell et al. analyzed corneal specimens obtained during surgery from patients with macular corneal dystrophy. Hassell et al. found that cells from normal corneas synthesized both a chondroitin sulfate proteoglycan and a keratan sulfate proteoglycan similar to those present in monkey and bovine corneas. Cells in macular corneal dystrophy synthesized a normal chondroitin sulfate proteoglycan, but did not synthesize either keratan sulfate or a mature keratan sulfate proteoglycan. Instead, the cells synthesized a glycoprotein with an unusually large oligosaccharide side chain.

The transparency of the cornea may be altered in a manner more subtle than that seen in the corneal traumas described above. In certain situations the appearance of optical, monochromatic aberrations may decrease the visual acuity (VA) of a subject's eye. On the basis of the mosaic structures of the retina, the visual acuity of the human eye could be 20/10 or better; however, such good acuity is rarely obtained. Two optical conditions account for the sub-optimal level of visual acuity are: diffraction due to pupil size and monochromatic aberrations. The limitations of visual acuity caused by diffraction decreases with increasing pupil diameter and may play an important role only for pupils smaller than 2 mm. The optical errors of higher order (aberrations) of the human eye, however, demonstrate an opposite behavior and may increase with larger pupil diameter.

The shape of the human cornea and lens is naturally designed in a way that these aberrations are minimized. To our knowledge, the monochromatic aberrations of the human eye so far have not been studied systematically in large series of individuals. Therefore, average values for a standard population are not available. However, loss of visual acuity through the introduction of optical aberrations may become clinically relevant with the advent of refractive corrective surgery.

Refractive surgery for myopia and astigmatism, such as radial keratotomy (RK), photorefractive keratectomy (PRK), and laser in situ keratomileusis (LASIK), induce a non-physiological corneal shape with a flat central area and increasing power towards the periphery. This shape induces an increase in optical aberrations and may lead to visual losses that are detected under low lighting conditions, and by low contrast visual acuity testing. These side effects of corneal refractive surgery have the potential for public health problems of a yet unknown discussion.

Comparison of corneal wavefront aberrations after PRK and LASIK has been compared in a prospective randomized study of 22 patients with bilateral myopia who received PRK on one eye and LASIK in the other eye. Before surgery, simulated papillary dilation from 3 mm to 7 mm caused a five to six fold increase in the total aberrations. After surgery, the same dilation resulted in a 25 to 32 fold increase in the total aberrations in the PRK group and a 28 to 46 fold increase in total aberrations in the LASIK. Both photorefractive keratectomy and laser in situ keratomileusis significantly increased the total wavefront aberrations and the values did not return to the preoperative level throughout the 12-month follow-up period.

Corneal wound healing study in rabbits following LASIK to evaluate the corneal wound healing process was followed for 1, 2 and 9 months past LASIK surgery. Periodic histopathological evaluation of the rabbit corneas showed disorganized collagen fibers along the interface of the corneal flap even 9 months after the LASIK surgery. These results show that the corneal aberrations and the wound healing process induced by the LASIK surgery continued at 9 months after LASIK. The methods and compositions of the invention disclosed herein provide the means with which to overcome the optical aberration side-effect of modern refractive surgical techniques.

Without being restricted to any particular mechanism of action, it has been theorized that the various corneal aberrations resulting from RK, PRK, LASIK, LASEK and other surgical procedures result from corneal collagen disorganization that occurs during the healing process. For example, following the LASIK procedure, after the flap is positioned to cover the site of the surgical procedure, corneal collagen will be formed to seal the incision. As this collagen is formed it is thought to be arraigned in a conformation that is, to one degree or another, less organized than the collagen located in areas of the cornea not affected by the surgery. Reorganization of this material would lead to a reduction in optimal aberrations resulting from such surgeries.

Accordingly, the present invention provides a new chemical method for the elimination of corneal aberrations and corneal collagen fiber disorganization resulting from accidental traumatic injury to the cornea or from refractive surgery for myopia, hyperopia and astigmatism, such as radial keratotomy (RK), photorefractive keratectomy (PRK), and laser in situ keratomileusis (LASIK), laser epithelial keratomileusis (LASEK) so as to improve visual acuity and quality of vision.

Non-Surgical Treatment of Pterigium

The present invention provides a new method for treating corneal pterigia by administering to the cornea an agent selected from: urea, a urea derivative, non-enzymatic protein urea, non-enzymatic proteins, nucleosides, nucleotides and their derivatives (e.g., adenine, adenosine, cytosine, cytadine, guanine, guanitadine, guanidine, guanidinium chloride, guanidinium salts, thymidine, thymitadine, uradine, uracil, cysteine), reduced thioctic acid, uric acid, calcium acetyl salicylate, ammonium sulfate or other compounds capable of causing non enzymatic dissolution of the proteoglycans or any possible combination thereof, in an amount that is effective to inhibit expression of MMP-1 and MMP-3 by fibroblasts. For example, one may administer to a corneal pterigium a therapeutically effective amount of an aqueous solution of urea or a urea derivative so as to stop or slow the expression of MMP-1 and MMP-3 by fibroblasts within the cornea. The urea and urea derivatives have the ability of deactivating the enzymatic activity of the expressed MMP's. It is also recognized and documented that urea and urea derivatives by their ability to solubilize proteins will change the secondary and tertiary structure of proteins thus inactivating these proteins. The resulting solubilization of proteins by Urea and Urea derivatives will clear corneal pterigia, stop the dissolution of the Bowman's layer and stop and produce regression of corneal Neovascularization of the cornea.

Several important clinical and pathological characteristics of primary and recurrent pterigia have been identified. These include the following:

a) UV-B radiation appears to be an etiologic agent for pterigia and limbal tumors.
b) Pterigia begin growing from limbal epithelium and not conjunctival epithelium
c) A segment of the limbal epithelium invades the cornea centripetally followed by conjunctival epithelium.
d) A distinct type of corneal cells develops at the leading edge of the pterigia tissue.
e) Bowman's layer is dissolved under the leading edge of the pterigia.
f) Vascularization occurs in the conjunctiva adjacent to the pterigia.
g) Pterigia have a high recurrence rate.

As in most normal, resting tissues, conjunctival-limbal-corneal epithelial tissue expresses very small amounts of MMP's that are nearly undetectable by immunohistochemistry techniques. However, it has been demonstrated lately that the altered limbal basal epithelial cells of pterigia express 6 MMP's of various types similar to other invasive tumors. It is speculated that these MMP's are likely promoters of the corneal invasion of this tumor and contribute to the dissolution of Bowman's layer. Elevated expression of both MMP-2 and MMP-9 are known to dissolve basement membrane components, such as hemidesmosomes, leading to migration and invasion of tumor cells. In addition four different groups of fibroblasts were identified in pterigia. These fibroblasts expressed mainly MMP-1 and some MMP-3.

Pterigia are tumors of altered limbal basal cells that secrete TGF-β and produce various types of MMP's similar to other invasive tumors. The tumor cell proteases degrade components of their basement membranes, which facilitate invasion. The pterigium cells invade over the Bowman's layer producing elevated MMP-1, MMP-2 and MMP-9 which contribute to the complete dissolution of Bowman's layer. Local fibroblasts are activated by the TGF-β and bFGF cytokine pathways to help complete the dissolution of the Bowman's layer by MMP-1.

Treatment of Corneal and Iris Neovascularization

The present invention provides a new method for treating corneal pterigia by administering to the cornea an agent selected from: urea, a urea derivative, non-enzymatic protein urea, non-enzymatic proteins, nucleosides, nucleotides and their derivatives (e.g., adenine, adenosine, cytosine, cytadine, guanine, guanitadine, guanidine, guanidinium chloride, guanidinium salts, thymidine, thymitadine, uradine, uracil, cysteine), reduced thioctic acid, uric acid, calcium acetyl salicylate, ammonium sulfate or other compounds capable of causing non enzymatic dissolution of the proteoglycans or any possible combination thereof, in an amount that is effective to inhibit neovascularization of the cornea and/or iris.

Under conditions of metabolic and injury-related stress, the cornea may be invaded by leucocytes and fibrocytes, the nutritive supply and metabolic reserves may become inadequate, with the result that new vessels sprout from the limbal plexus and grow into the stroma, thus resulting in corneal vascularization. The nature of the stimulus to ingrowth of vessels has been associated with the loosening of the tissue associated with the injury and the resulting of corneal edema. However, the primary factor of corneal new vascularization is associated with the buildup and release of pharmacologically active angiogenic compounds like VEGF and FGF that are responsible for the formation of new vessels so as to supply the needs of the cornea. The presence of new blood vessels in the cornea makes the cornea full of vessels and interferes with the visual acuity of the patient. In a similar fashion, injuries in the posterior part of the eye and reduction of supply of oxygen to the retina and the optic nerve, unleashes the buildup of VEGF angiogenic factors in the vitreous. The result is the new vessel formation in the iris, causing bleeding and blindness.

Treatment of Glaucoma

The present invention provides methods for treating glaucoma by administering topically onto the eye or by injection into the eye (e.g. intravitreal, intrastromal or sub-conjunctival injection) a therapeutically effective amount of an aqueous solution containing an agent selected from: urea, a urea derivative, non-enzymatic protein urea, non-enzymatic proteins, nucleosides, nucleotides and their derivatives (e.g., adenine, adenosine, cytosine, cytadine, guanine, guanitadine, guanidine, guanidinium chloride, guanidinium salts, thymidine, thymitadine, uradine, uracil, cysteine), reduced thioctic acid, uric acid, calcium acetyl salicylate, ammonium sulfate or other compounds capable of causing non enzymatic dissolution of the proteoglycans or any possible combination thereof.

As well as being an important marker of the presence and advancement of glaucoma, the structure of the optic nerve head may play a role in the pathogenesis of glaucoma. Two main theories exist for the mechanism of optic nerve damage in glaucoma. First, the mechanical IOP related theory suggests that the pressure head acts directly on the lamina cribosa. The lamina cribosa is not supported well superiorly and inferiorly at the disk and it is here that the initial damage occurs to produce the characteristic arcuate defects. Variations in the ganglion cell support at the disk may explain the variations between IOP susceptibilities of individuals with similar IOP's. Second is the vascular mechanism theory, which posits that changes within the microcirculation of the disk capillaries are responsible for glaucomatous changes. whether this is primarily vascular or secondary to IOP has not been elucidated.

The present invention provides urea containing solutions (e.g., solutions which contain urea, a urea derivative (e.g. hydroxyurea) and/or mixtures thereof) that may be topically applied or are injected into the eye. Additionally, some of the urea-containing topical or injectable solutions of the present invention may further contain antimetabolite(s) (e.g. mitomicyn C, methotrexate, 6-mercaptopurine, thioguanine, 5-fluorouracil, cytosine arabinoside and 5-azacytidine).

Solutions of urea or hydroxyurea, which have been adjusted to a pH of approximately 4.0 to 8.0 are substantially non-toxic and well tolerated when administered topically, or by intravitreal, intrastromal and conjunctival injection, one (1), two (2) or more times, in a volume of 15 to 200 microliters per application, at doses of 0.001% to 4.0% and also doses of 0.001% to 20.0% of urea.

EXAMPLES OF STABLE AQUEOUS UREA FORMULATIONS

The following are examples of urea containing solutions that are usable in accordance with this invention:

| Example 1 | |
|---|---|
| Urea USP/NF | 0.001-4.0% |
| Sodium Chloride USP/NF | 0.1%-0.9% |
| Sterile Water for Injection USP | Q.S. 100% |
| pH of the solution | 4.0-8.0 |
| (Adjust pH using 0.1N HCl or 0.1N NaOH) | |
| Example 2 | |
| Urea USP/NF | 0.001-4.0% |
| Citric Acid USP/NF | 0.00007%-0.02% |
| Sodium Chloride USP/NF | 0.1%-0.9% |
| Sterile Water for Injection USP | Q.S. 100% |
| pH of the solution | 4.0-8.0 |
| (Adjust pH using 0.1N HCl or 0.1N NaOH) | |
| Example 3 | |
| Urea USP/NF | 0.001-4.0% |
| Citric Acid USP/NF | 0.00007%-0.02% |
| Sterile Water for Injection USP | Q.S. 100% |
| pH of the solution | 4.0-8.0 |
| (Adjust pH using 0.1N HCl or 0.1N NaOH) | |
| Example 4 | |
| Urea USP/NF | 0.01-20.0% |
| Sodium Chloride USP/NF | 0.1%-0.9% |
| Sterile Water for Injection USP | Q.S. 100% |
| pH of the solution | 4.0-8.0 |
| (Adjust pH using 0.1N HCl or 0.1N NaOH) | |
| Example 5 | |
| Urea USP/NF | 0.01-20.0% |
| Citric Acid USP/NF | 0.00007%-0.02% |
| Sodium Chloride USP/NF | 0.1%-0.9% |
| Sterile Water for Injection USP | Q.S. 100% |
| pH of the solution | 4.0-8.0 |
| (Adjust pH using 0.1N HCl or 0.1N NaOH) | |

| Example 6 | |
|---|---|
| Urea USP/NF | 4.0% |
| Potassium Phosphate Dibasic USP/NF | 5.0 millimolar |
| Sterile Water for Injection USP | Q.S. 100% |
| pH of the solution | 4.0-8.0 |
| (Adjust pH using 0.1N HCl or 0.1N NaOH) | |
| Example 7 | |
| Urea USP/NF | 4.0% |
| Potassium Phosphate Dibasic USP/NF | 50.0 millimolar |
| Sterile Water for Injection USP | Q.S. 100% |
| pH of the solution | 4.0-8.0 |
| (Adjust pH using 0.1N HCl or 0.1N NaOH) | |
| Example 8 (Lyophilized Powder) | |
| Urea USP/NF | 0.01%-20.0% |
| Sorbitol USP/NF | 0.10%-0.50% |
| Citric Acid USP/NF | 0.00007%-0.02% |
| Sterile Water for Injection USP | Q.S. 100% |
| pH of the solution | 4.0-8.0 |
| (Adjust pH using 0.1N HCl or 0.1N NaOH) | |
| Example 9 | |
| Urea USP/NF | 4.0% |
| Sorbitol USP/NF | 0.10% |
| Sterile Water for Injection USP | Q.S. 100% |
| pH of the solution | 4.0-8.0 |
| (Adjust pH using 0.1N HCl or 0.1N NaOH) | |

Citrate, phosphate or other buffers may alternatively be used in the above-listed formulations of Examples of 1-7. Also, sodium chloride, dextrose or other alternative bulking agents could be used in these formulations.

EXAMPLES OF AQUEOUS UREA SOLUTIONS CONTAINING ALCOHOLS AND BLOCK POLYMERIC

| Example 10 | |
|---|---|
| Urea USP/NF | 0.01%-20.0% |
| Isopropyl Alcohol (90%) | 0.5%-20% |
| Sodium Chloride USP/NF | 0.1%-0.9% |
| Citric Acid USP/NF | 0.00007%-0.02% |
| Sterile Water for Injection USP | Q.S. 100% |
| pH of the solution | 4.0-8.0 |
| (Adjust pH using 0.1N HCl or 0.1N NaOH) | |
| Example 11 | |
| Urea USP/NF | 0.01%-20.0% |
| Isopropyl Alcohol (90%) | 0.5%-20% |
| Sterile Water for Injection USP | Q.S. 100% |
| pH of the solution | 4.0-8.0 |
| (Adjust pH using 0.1N HCl or 0.1N NaOH) | |
| Example 12 | |
| Urea USP/NF | 0.01%-20.0% |
| Isopropyl Alcohol (90%) | 0.5%-20% |
| Propylene Glycol | 0.10%-50.0% |
| Citric Acid USP/NF | 0.00007%-0.02% |
| Sterile Water for Injection USP | Q.S. 100% |
| pH of the solution | 4.0-8.0 |
| (Adjust pH using 0.1N HCl or 0.1N NaOH) | |
| Example 13 | |
| Urea USP/NF | 0.01%-20.0% |
| Propylene Glycol | 0.10%-50.0% |
| Citric Acid USP/NF | 0.00007%-0.02% |
| Sterile Water for Injection USP | Q.S. 100% |
| pH of the solution | 4.0-8.0 |
| (Adjust pH using 0.1N HCl or 0.1N NaOH) | |

| Example 14 | |
|---|---|
| Urea USP/NF | 0.01%-20.0% |
| Polyethylene Glycol | 0.10%-50.0% |
| Sodium Chloride USP/NF | 0.10%-0.90% |
| Sterile Water for Injection USP | Q.S. 100% |
| pH of the solution | 4.0-8.0 |
| (Adjust pH using 0.1N HCl or 0.1N NaOH) | |

EXAMPLES OF AQUEOUS HYDROXYUREA SOLUTIONS

The following are examples of hydroxyurea-containing formulations useable in accordance with the present invention.

| Example 15 | |
|---|---|
| Hydroxyurea USP/NF | 4.0% |
| Sodium Chloride USP/NF | 0.10%-0.90% |
| Citric Acid USP/NF | 0.00007%-0.02% |
| Sterile Water for Injection USP | Q.S. 100% |
| pH of the solution | 4.0-8.0 |
| (Adjust pH using 0.1N HCl or 0.1N NaOH) | |

| Example 16 | |
|---|---|
| Hydroxyurea USP/NF | 4.0% |
| Sodium Chloride USP/NF | 0.10%-0.90% |
| Sterile Water for Injection USP | Q.S. 100% |
| pH of the solution | 4.0-8.0 |
| (Adjust pH using 0.1N HCl or 0.1N NaOH) | |

| Example 17 | |
|---|---|
| Hydroxyurea USP/NF | 0.01%-15.0% |
| Sodium Chloride USP/NF | 0.10%-0.90% |
| Sterile Water for Injection USP | Q.S. 100% |
| pH of the solution | 4.0-8.0 |
| (Adjust pH using 0.1N HCl or 0.1N NaOH) | |

| Example 18 | |
|---|---|
| Hydroxyurea USP/NF | 4.0% |
| Potassium Phosphate Dibasic USP/NF | 5.0-50.0 millimolar |
| Sterile Water for Injection USP | Q.S. 100% |
| pH of the solution | 4.0-8.0 |
| (Adjust pH using 0.1N HCl or 0.1N NaOH) | |

| Example 19 | |
|---|---|
| Hydroxyurea USP/NF | 4.0% |
| Sorbitol USP/NF | 0.10%-0.50% |
| Citric Acid USP/NF | 0.00007%-0.02% |
| Sterile Water for Injection USP | Q.S. 100% |
| pH of the solution | 4.0-8.0 |
| (Adjust pH using 0.1N HCl or 0.1N NaOH) | |

EXAMPLES OF AQUEOUS ANTIMETABOLITE FORMULATIONS

The following are examples of formulations for Antimetabolite solutions that are usable in accordance with the present invention. To treat a patient's eye with the a combination of antimetabolite and urea or another agent of the present invention, these antimetabolite solutions may be combined with the aqueous solution of urea or other agent or the antimetabolite solution may be administered topically or injected separate from the aqueous solution of urea or other agent.

| Example 20 | |
|---|---|
| Hydroxyurea USP/NF | 0.01%-15.0% |
| Sodium Chloride USP/NF | 0.10%-0.90% |
| Citric Acid USP/NF | 0.00007%-0.02% |
| Sterile Water for Injection USP | Q.S. 100% |
| pH of the solution | 4.0-8.0 |
| (Adjust pH using 0.1N HCl or 0.1N NaOH) | |

| Example 21 | |
|---|---|
| Mitomycin C | 100 μg-200 mg |
| Sodium Chloride USP/NF | 0.10%-0.90% |
| Citric Acid USP/NF | 0.00007%-0.02% |
| Sterile Water for Injection USP | Q.S. 100% |
| pH of the solution | 4.0-8.0 |
| (Adjust pH using 0.1N HCl or 0.1N NaOH) | |

| Example 22 | |
|---|---|
| Thiourea | 0.010%-10.0% |
| Sodium Chloride USP/NF | 0.10%-0.90% |
| Citric Acid USP/NF | 0.00007%-0.02% |
| Sterile Water for Injection USP | Q.S. 100% |
| pH of the solution | 4.0-8.0 |
| (Adjust pH using 0.1N HCl or 0.1N NaOH) | |

| Example 23 | |
|---|---|
| Thiourea | 0.010%-10.0% |
| Sterile Water for Injection USP | Q.S. 100% |
| pH of the solution | 4.0-8.0 |
| (Adjust pH using 0.1N HCl or 0.1N NaOH) | |

What is claimed is:

1. A method for refractive correction in the eye of a human or veterinary patient, said method comprising the steps of:
   (A) delivering by topical application onto or by intrastromal or sub-conjunctival injection of the eye, a therapeutically effective amount of an agent that comprises a material selected from the group consisting of urea, hydroxyurea and thiourea in an amount that is effective to soften the cornea; and
   (B) modifying the shape of the softened cornea in a manner that results in a desired refractive correction.

2. A method according to claim 1 wherein said agent is delivered to the cornea by topical application.

3. A method according to claim 1 wherein said agent is delivered to the cornea by an injection technique selected from the group consisting of intrastromal injection, injection into the Anterior chamber and sub-conjunctival injection.

4. A method according to claim 1 wherein the agent delivered in Step A comprises 30 micrograms-7500 micrograms of urea per 50 microliters to 100 microliters of solution.

5. A method according to claim 1 wherein the solution delivered in Step A comprises approximately 300 micrograms of urea per 50 microliters of solution.

6. A method according to claim 1 wherein Step A delivers a dose of 0.01% to 15.0% urea onto the cornea of the eye.

7. A method according to claim 1 wherein the agent administered in Step A further comprises at least one antimetabolite agent.

8. A method according to claim 1 wherein the agent administered in Step A further comprises at least one polyglycol agent.

9. A method according to claim 1 wherein the method is performed to treat a vision disorder selected from the group consisting of: myopia, presbyopia, hyperopia, astigmatism and keratoconus.

10. A method according to claim 1 wherein Step B comprises placing a rigid contact lens on the eye.

* * * * *